United States Patent [19]

Carter

[11] Patent Number: 5,661,538
[45] Date of Patent: Aug. 26, 1997

[54] PORTABLE SELF-MEASUREMENT PUPILLOMETER WITH ACTIVE OPTO-ELECTRONIC CENTERING AID AND METHOD FOR USE THEREOF

[75] Inventor: Elbert P. Carter, Wilmington, Del.

[73] Assignee: Fairville Medical Optics, Inc., Mendenhall, Pa.

[21] Appl. No.: 559,513

[22] Filed: Nov. 15, 1995

[51] Int. Cl.⁶ .................................. A61B 3/02; A61B 3/00
[52] U.S. Cl. ........................ 351/237; 351/222; 351/246
[58] Field of Search ........................ 351/211, 221, 351/206, 205, 237, 239, 243, 245, 246

[56] References Cited

U.S. PATENT DOCUMENTS 4,800,404  1/1989  Ginsburg et al. ................ 351/243
5,187,506  2/1993  Carter ............................... 351/221

*Primary Examiner*—Hung X. Dang
*Attorney, Agent, or Firm*—Duane, Morris & Heckscher

[57] ABSTRACT

Pupillometers with semi-passive targets. The semi-passive targets allow a user of the pupillometer to center the user's pupil on an optically sensitive element in the pupillometer to characterize the pupil. Preferably, a set of centering diodes is disposed on a familiar, easily recognized target which is activated by the optico-electronic means to give the user an indication when the pupil has been centered on the optically sensitive element and that the user has centered the pupil on the defined portion of the passive target.

18 Claims, 9 Drawing Sheets

| FIG. 4 | |
|---|---|
| FIG. 4A | FIG. 4C |
| FIG. 4B | FIG. 4D |

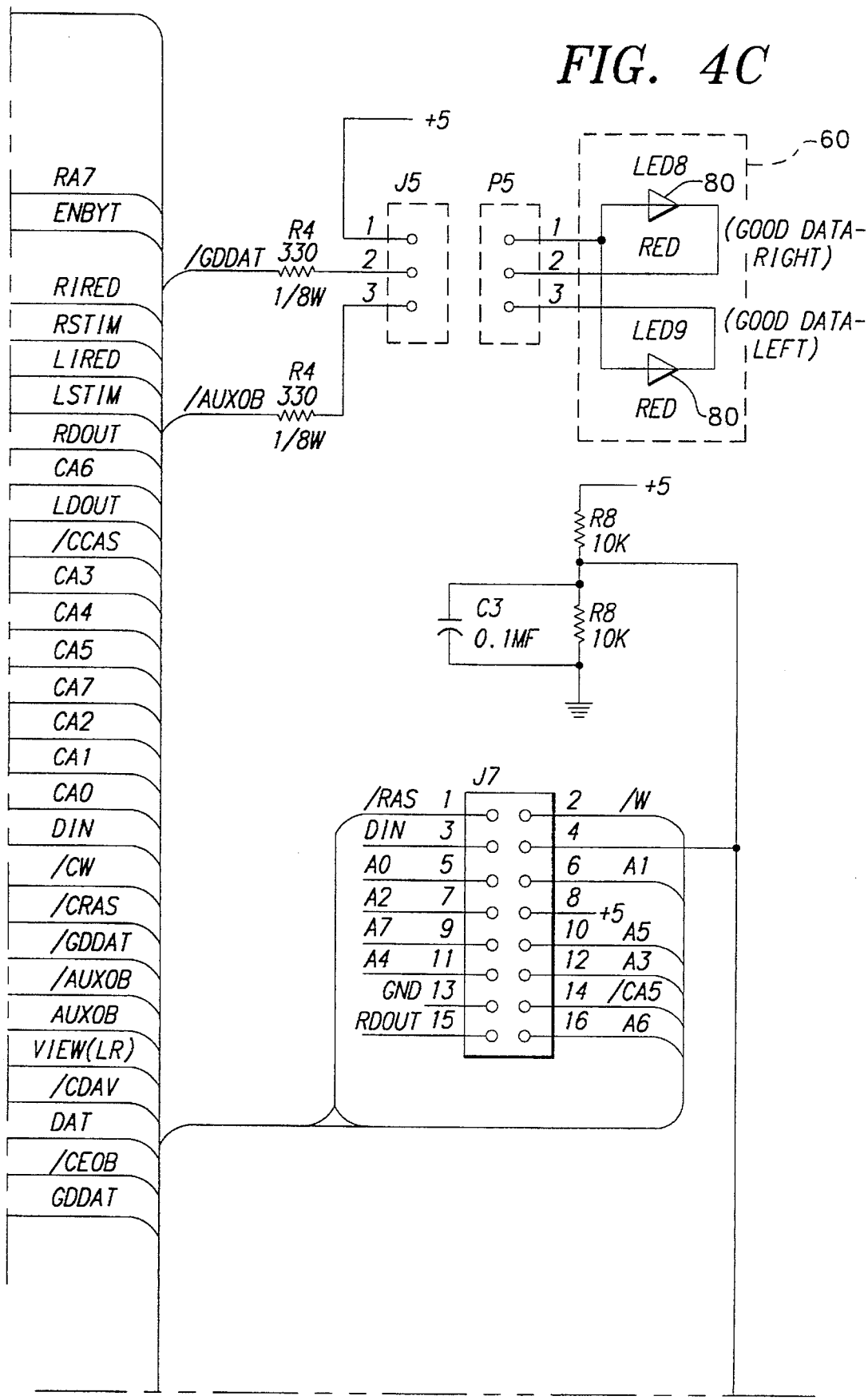

PORTABLE SELF-MEASUREMENT PUPILLOMETER WITH ACTIVE OPTO-ELECTRONIC CENTERING AID AND METHOD FOR USE THEREOF

FIELD OF THE INVENTION

This invention relates generally to pupillometers for imaging and measuring a user's pupil. More specifically, this invention relates to portable pupillometers and methods of semi-passive target pupillometry wherein the pupillometer includes passive or near passive means for aiding a user of the pupillometer to center the pupil for imaging or characterization.

BACKGROUND OF THE INVENTION

Pupillometry has been discovered to be an effective and useful non-invasive means of characterizing a subject's pupillary response and the condition of the human and animal autonomic nervous system. For example, in U.S. Pat. No. 5,187,506, Carter, it was disclosed therein that narcotics, opiates, depressants, stimulants, alcohol, and both legal and illegal drugs may produce deleterious and destructive effects on an individual's mental and physical performance. Pupillometry as described in the aforementioned patent is useful in detecting such drug or alcohol impairment. The teachings of U.S. Pat. No. 5,187,506, Carter, are specifically incorporated herein by reference. Another useful and effective pupillometer is described in U.S. Pat. No. 4,755,043, Carter. This patent describes a portable, hand-held, dynamic, automatic scanning pupillometer which is operated by a user to view a subject's pupil, thereby obtain pupil images and to measure pupil size and dynamic reaction to a light stimulus. The teachings of U.S. Pat. No. 4,755,043 are also incorporated herein by reference.

A main difference between the Carter '506 patent and the Carter '043 patent is that the pupillometer of the Carter '506 patent is a desktop or other mechanically supported device which may be totally operated by an alert person whose pupil is to be imaged, while the Carter '043 patent teaches a pupillometer which is operated by a user and can be used to image the pupil of a subject in any posture and any state of alertness or consciousness. A distinct advantage of the pupillometer described in the Carter '506 patent is the incorporation of a self-centering means therein so that the user can easily and quickly center the image of the pupil on an image sensor to form an image thereof. The pupillometer of the '043 patent does not incorporate such a convenient aid to centering, and therefore an operator must painstakingly position the device to center the pupil to obtain an image thereof. The pupillometer of the Carter '506 patent employs a unique electronic centering means which allows the user to center the pupil on an optical semiconductive device in the optical block of the pupillometer by displaying an image of the pupil on a display device at the center of the user's field of view. This centering means has the disadvantage, however, that to the novice user, the pupil image is an unfamiliar, strange and poorly understood image and its movement relative to the user's gaze and head position can cause frustration and anxiety. This centering means also has the advantage of allowing an observer supervising the use of the instrument to coach the user during the centering process by referring to a duplicate of the pupil image displayed on the monitor of the host computer. This computer monitor image also allows the supervisor to judge from the shape and position of the pupil image whether a dropping eyelid or eyelashes are likely to degrade the measurement of pupil size and reactivity. Thus, on many occasions, the pupillometer of the Carter '506 patent while easy for the experienced user to operate, is simply inadequate to efficiently provide adequate pupil imaging and characterization for novice users such as subjects in clinical examinations.

Because of these aforementioned problems and deficiencies, the inventor of the subject matter herein claimed and disclosed has discovered that existing portable and tabletop pupillometers fail to solve needs in the art for compact, portable devices which provide efficient and easy to understand and use centering means under varied conditions of use. The aforementioned pupillometers do not provide the advantageous combination of compact size with centering aids to facilitate their use and therefore, do not fulfill a long-felt need in the art for a pupillometer to make rapid, accurate and reliable measurement of pupil size and reactivity while requiring minimum instruction and training of novice users.

SUMMARY OF THE INVENTION

The aforementioned problems are solved and long-felt needs met by pupillometers provided in accordance with the present invention. The pupillometers preferably comprise optical means for bussing light to a user's pupil, centering means for outputting light to the user's eye through the optical means to allow the user to center an image of the pupil on an element in the optical means, and target means in optical contact with the optical means and further interfaced with the centering means for providing an orientation for the user when the user observes the centering means, thereby allowing the user to center the image of the pupil on the element in the optical means.

Methods of characterizing a pupil provided in accordance with the present invention also solve the aforementioned long-felt needs. The methods preferably comprise focusing the eye containing the pupil on a passive target, an activating and indicator mechanism which will indicate that the pupil is adequately centered on the passive target, and irradiating the pupil with characterizing radiation during a predetermined automatic measurement cycle when the indicator mechanism indicates that the pupil is centered.

The pupillometers and methods of pupillometry described herein greatly reduce the difficultly of centering pupils for pupil characterization, imaging and sizing, particularly for subjects whose naked eye visual acuity is not at the level required for other, more visually demanding centering aids. The pupillometers and methods claimed and described also greatly reduce pupillometer costs, since the electronic circuits for driving pupillometers provided in accordance with the present invention are greatly simplified. This concomitantly reduces manufacturing and fabrication costs which have not heretofore been achievable in the pupillometry art.

The invention will be best understood by those with skill in the art by reading the following Detailed Description of Preferred Embodiments in conjunction with the drawings which are first described briefly below.

BRIEF DESCRIPTION OF THE DRAWINGS

FIGS. 4A through 4D are circuit schematics of the electronic scanning circuit for pupillometers provided in accordance with the present invention.

DETAILED DESCRIPTION OF THE PREFERRED EMBODIMENTS

Figure 1:
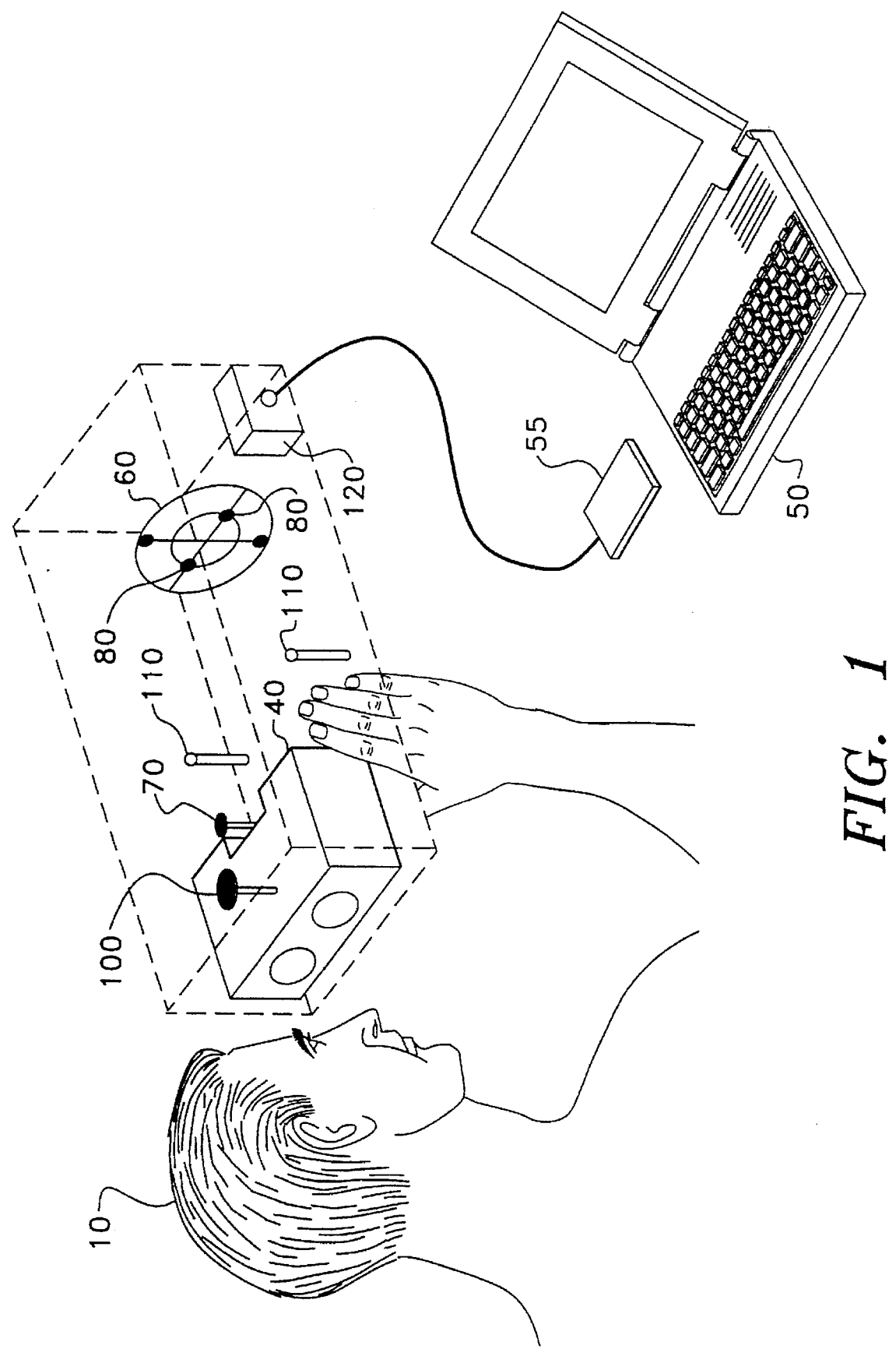
FIG. 1 is a schematic diagram of a pupillometer having a semi-passive target and a user utilizing the pupillometer provided in accordance with the present invention.

Referring now to the drawings wherein like reference numerals refer to like elements, FIG. 1 illustrates a pupillometer provided in accordance with the present invention wherein a subject or user 10 operates pupillometer 20. In its basic design, pupillometer 20 preferably comprises a casing 30 made out of a hardened plastic material or light-weight metal, thereby making the pupillometer easily portable and rugged. Within casing or housing 30, an optical block 40 contains the various optical elements which will focus light to and from the user's eye, and the photo-optical and electronic components which allow the pupillometer to provide an image of the pupil. A small electronic circuit board mounted directly on the optical block 40 contains the scanning and control electronics. Optical block 40 electronics are preferably interfaced to a personal computer 50 through an interface circuit board 55. Computer 50 uses special software for driving the optical block 40 and providing means to analyze data captured by the scanning circuit and data analysis to translate into, and display pupil data in, a usable and easily understood format. The software for driving the personal computer 50 is substantially similar to that found in the Carter '506 patent, the teachings of which have been specifically incorporated herein by reference.

The passive target 60 is mounted on the optical axis of the optical block 40. The target is illuminated by diodes 110 whose brightness may be adjusted by control 120 to suit differences in users' visual acuity and other conditions of use. The user 10 viewing that target through the optical block 40 positions his or her head and eye to center the image of the target 60 in the aperture or field of the optical block, thus placing the pupil of that eye on the optical axis of the optical block. In operation of the pupillometer 20 to be described below, this also centers the pupil's image on an optical element in the optical block 40. The terms "semi-passive" or "near passive" as used herein with reference to target 60 means that the fixation or centering target 60 does not move as in the means taught by the Carter '506 patent, nor itself emit or accept light or electronic inputs. Thus, target 60 is constructed of a material which can be printed or impressed with a target image of suitable color and design.

Figure 2:
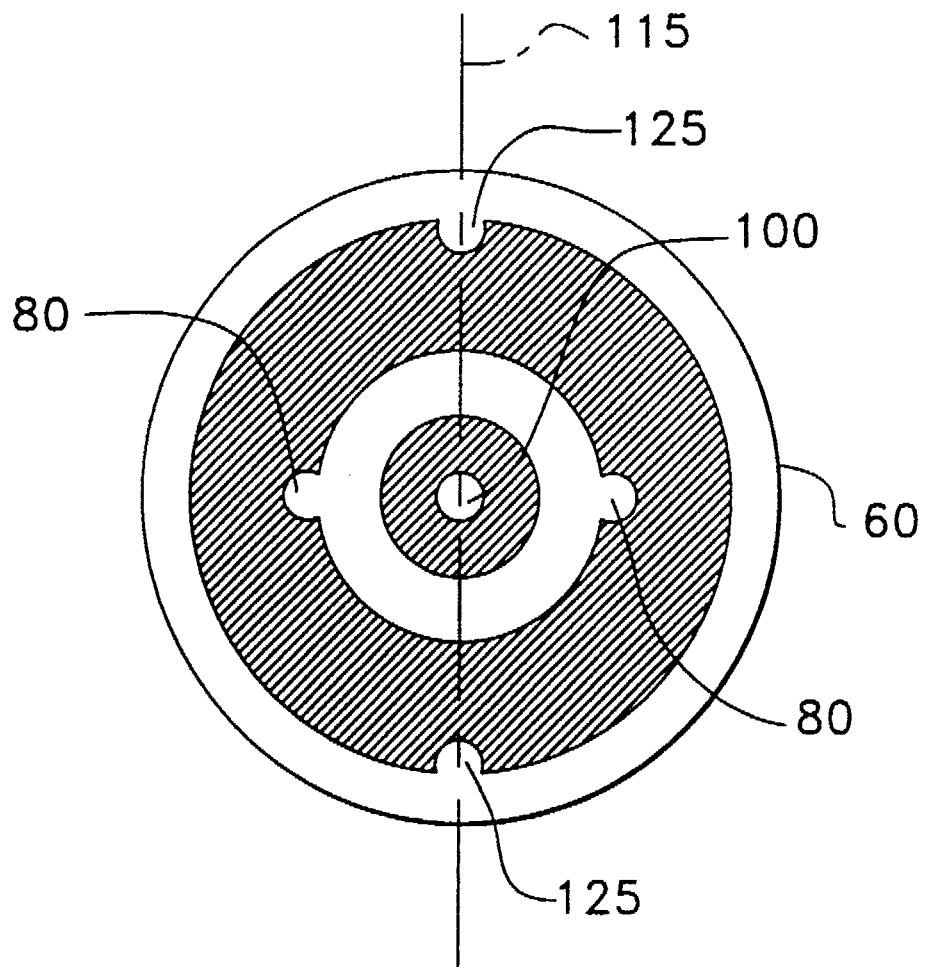
FIG. 2 is a schematic of a passive bull's eye target having interfaced thereon "good data" diodes for centering a pupil in accordance with the present invention.

Preferably, to operate pupillometer 20, the user activates a switch 70 or a person supervising the test may initiate operation from the host computer keyboard. This energizes a set of red light-emitting diodes (LEDs) shown generally at 80, allowing the user to center the pupil on the passive target 60 as will be described more fully hereafter. The user views target 60 through a set of binocular eyepieces 90. However, most preferably only one pupil is imaged at a time, and therefore an eye selector knob 100 is provided which is rotatable so that a mirror within the optical block isolates either the left or the right eye for centering on the target 60 and during imaging generally. The binocular eyepieces 90 contain stimulus diodes 140 which may be used to flash visible light on the user's pupil for a predetermined interval after he or she has centered the pupil on the target 60, thereby causing the pupil to react so that the pupil size and/or reaction to a visual stimulus may be recorded. Referring now to FIG. 2, a schematic diagram of the passive target is illustrated. In a most preferred embodiment, the passive target image is a "bull's eye" target, having a center bull's eye point 100. While other target configurations are possible, since a bull's eye is generally a familiar object understood by most people, the bull's eye pattern provides a good target for centering. When the user depresses the switch 70, the red LEDs 80 are activated so that the user can center the pupil on the target 60. In a preferred operation of the pupillometer described herein, the LEDs 80 are defined as "good data" diodes.

When the user 10 centers the image of the target 60 in the field of the optical block 40 and depresses the switch 70 scanning of the pupil with infrared radiation starts and the good data diodes are energized. If the centering is accurate both diodes are lit, and the user then can see that the pupil is centered. However, if the user moves too far to the left, for example, the left good data diode will go out, indicating that the eye is off the optical axis. Similarly, if the user moves his or her eye too far to the right, the pupil is off the optical axis and the right good data LED would go out.

When the user sees that both LEDs 80 are lit, indicating that the pupil is centered on the vertical axis 115, he or she releases switch 70 which causes the software to flash one of the set of stimulus diodes found in both the binocular eyepieces 90, causing the pupil to contract. A photo-optical element as substantially described in the Carter '506 patent, is read to extract diameters at pre-determined time intervals, thereby allowing capture of an array of pupil diameter and time data which are manipulated by the software to plot a pupil diameter versus time graph or pupil response curve on the host computer monitor. As is also taught by the Carter '506 patent, scanning and pupil characterization are accomplished during the 3-second interval after the stimulus diodes have been activated.

A set of IREDs 130 supply infrared radiation for imaging the pupil. When the infrared-emitting diodes irradiate the pupil and iris, infrared radiation is reflected back from the iris through a beam splitter in the optical block 40 which is then focused by the particular optical elements in the optical block to provide data to the computer 50 for pupil characterization. In still more preferred embodiments, the second set of red LEDs 125 is provided interfaced to the target on the vertical axis of the target to provide a further orientation for the user as he or she centers the pupil on the optical axis with horizontal centering diodes 80.

Figure 3:
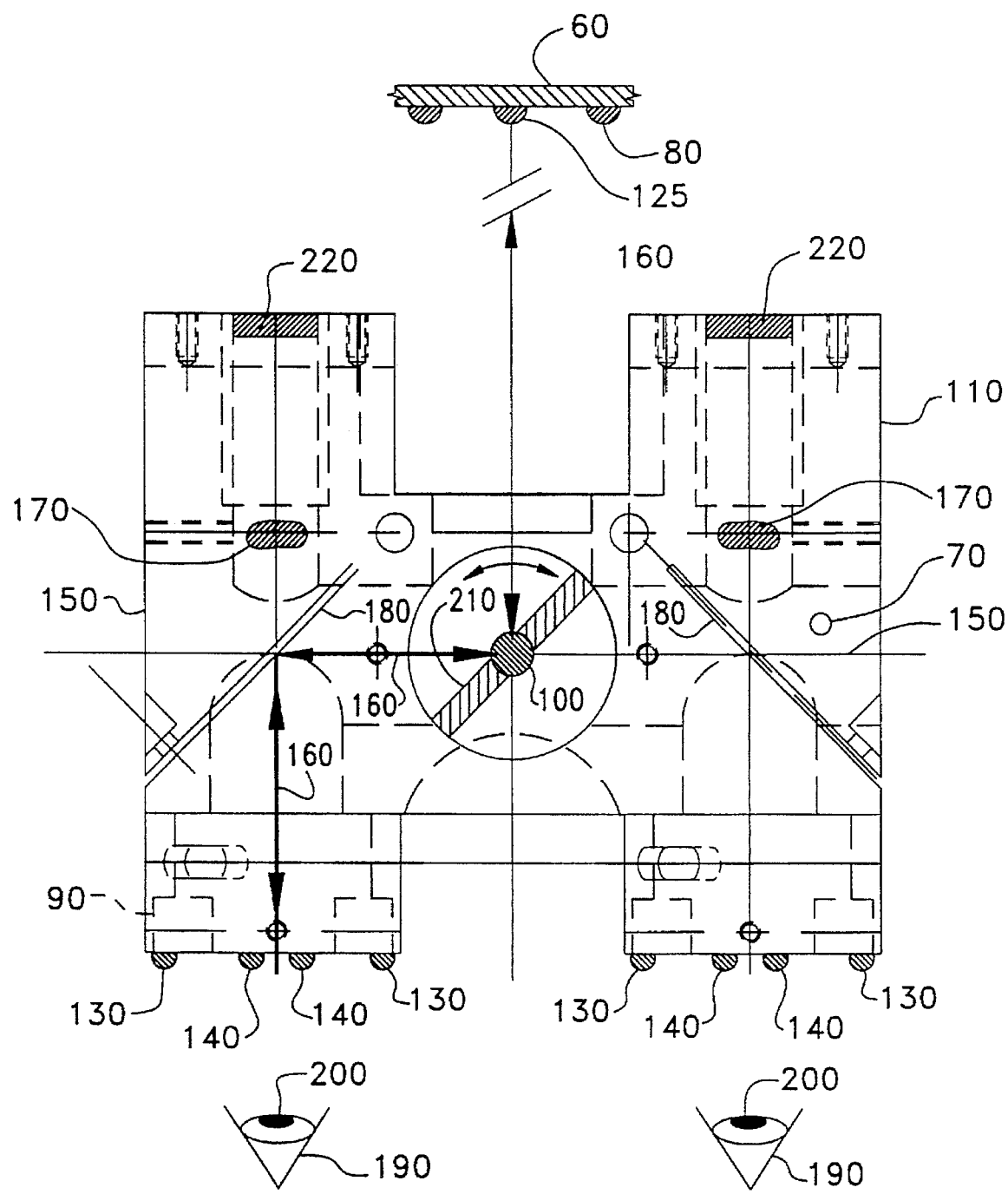
FIG. 3 is a schematic diagram of the optical block of pupillometers provided in accordance with the present invention.
Figure 4A:
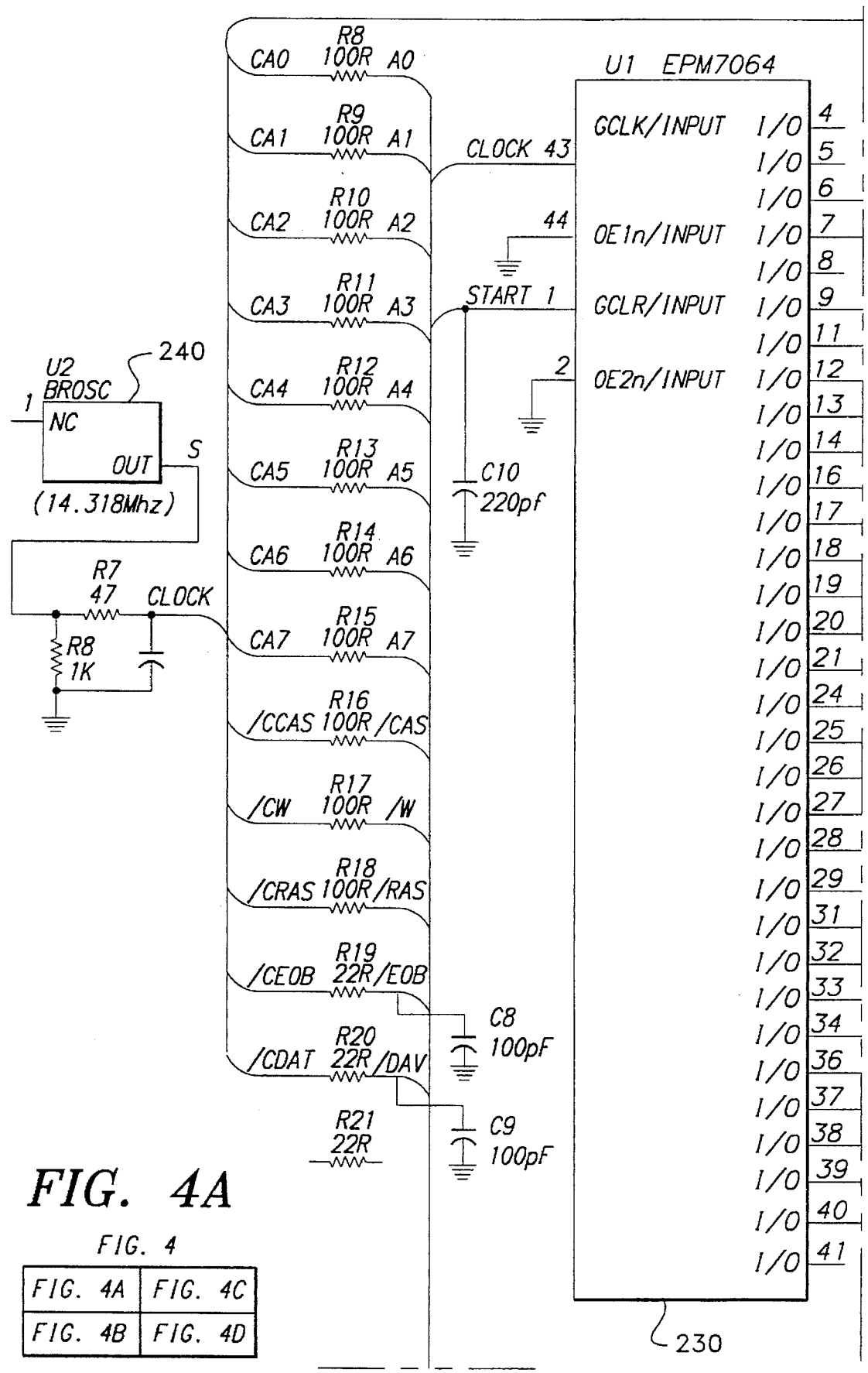
Figure 4B:
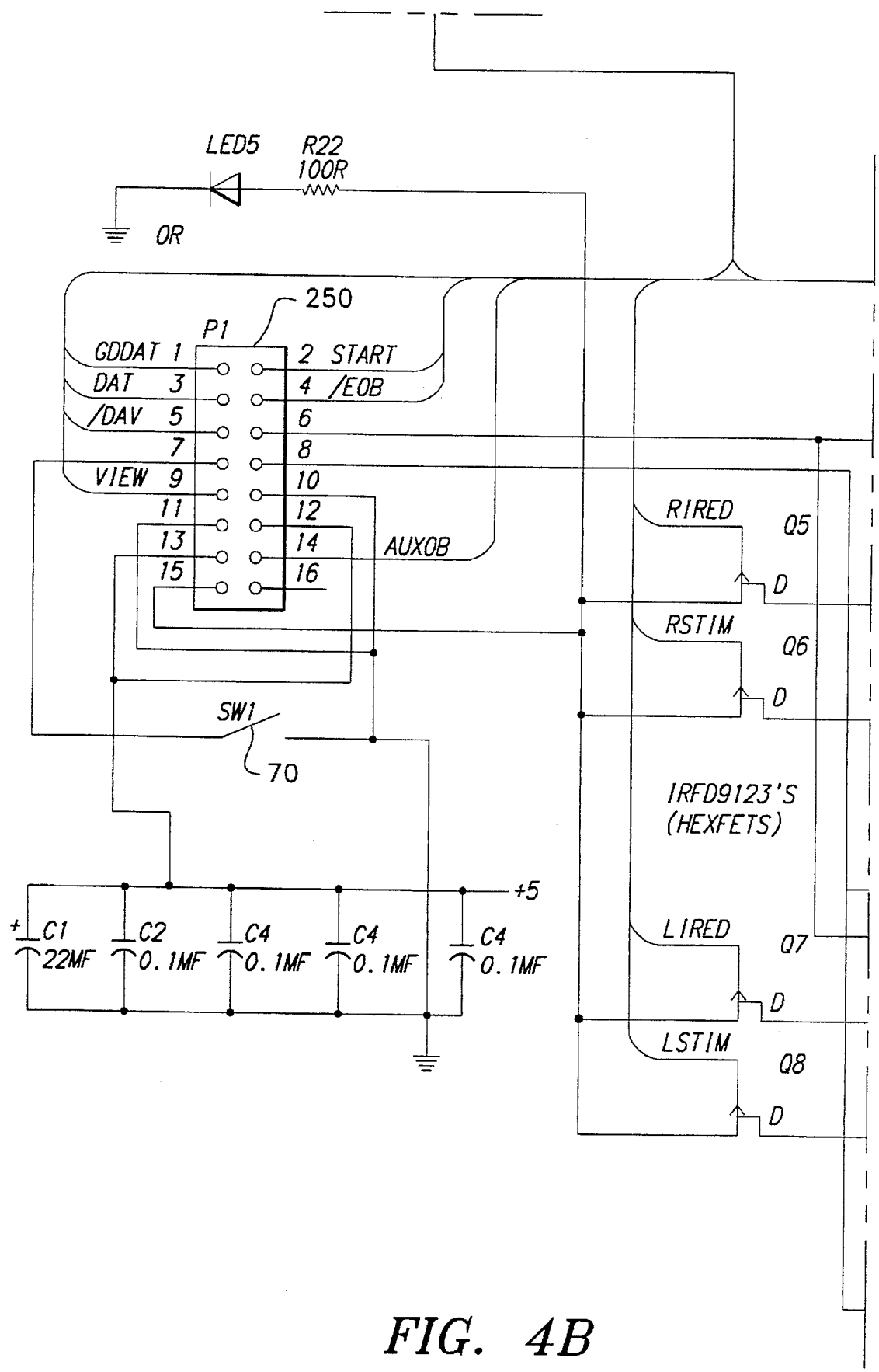
Figure 4D:
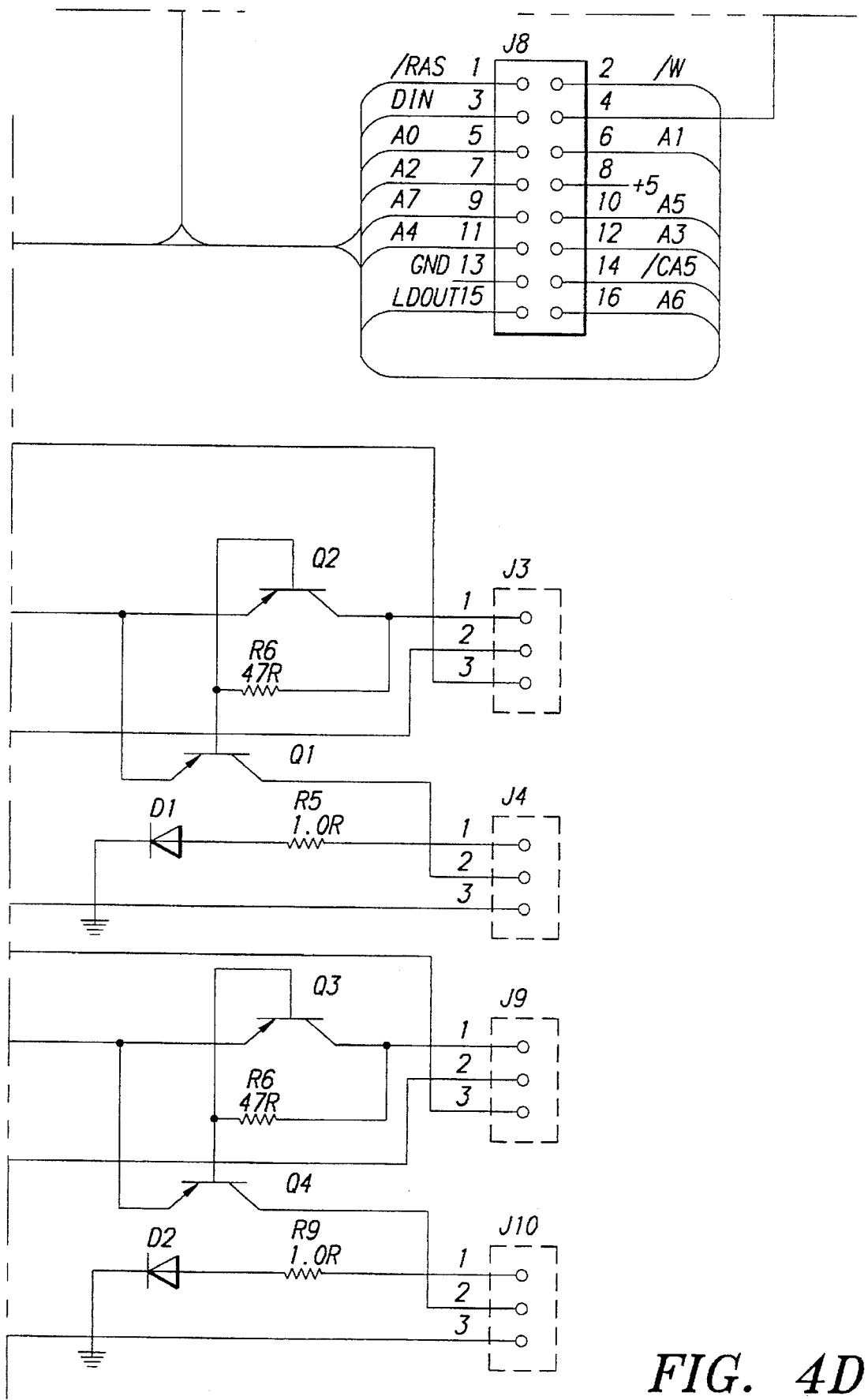

FIG. 3 illustrates the optical elements of optical block 40. The binocular eye pieces have interfaced thereon the stimulus diodes, preferably emitting a high intensity green light 140, and the infrared scanning diodes shown generally at 130. The user interfaces his or her eyes 190 on the binocular eyepieces such that the eye to be measured views down the bore 150 to target 60 along optical path 160 which traces the light path in the optical block both before and after reflection at dichroic mirror 180 and the rotatable mirror 210 as shown in the figure for the left eye. A set of lenses shown generally at 170 is interposed in barrels 150 to focus the user's pupil on the photo-optical elements 220. The dichroic mirrors 180 reflect the visible light from the target 60 but transmit the infrared light from diodes 140, to lenses 170 which focus images of the pupil on the photo-optical elements 220.

As shown in FIG. 3, the user places his or her eyes 190 against binocular eyepieces 90. Pupils 200 are then in a position to be scanned and imaged after being centered on target 60. A front surface mirror 210 is rotatably mounted in the optical path 160 and is rotatable by the eye selector or by means controlled by the software. During the centering procedure, light from the diodes 80 reflects against the mirror 210 onto dichroic mirror 180 which then falls back on the user's left eye so that the user sees an image of the passive target 60 with the bull's eye and the diodes 80 and 125. The infrared diodes 130 are continuously irradiating the pupil to tell the software and computer 50 the position of the pupil 200 with respect to the optical axis of the optical block 40.

In order to accomplish the electronic process of centering and scanning, a set of photo-optical elements 220 at the far end of the barrels 150 are connected to the optical block 40 circuit board. These photo-optical elements are preferably IS32A OpticRAMs which are commercially available and which form an image of the pupil by creating a pattern of pixels on the infrared irradiation sensitive RAM (random access memory). Thus, the pixel information is converted to electronic information and bussed to a computer interface board which is preferably a compact circuit board such as those conforming to the standards set by the Personal Computer Memory Card International Association (PCMCIA) having the particular timing and control electronics which are required for pupillometers provided in accordance with the present invention which are identical in function to those taught in U.S. Pat. Nos. 5,187,506 and 4,755,043.

When the user observes that the pupil is substantially centered on the target 60 and therefore on the pixel array on the OpticRAM 220, the red LEDs 80 will both remain on and the user releases the switch 70 which indicates to the software and computer 50 that the pupil may be stimulated by stimulus diodes 140 and pupil measurements taken for determining pupil size or pupil reaction to a light stimulus. In this manner, the pupil size can be measured as well as the pupil response during constriction and re-dilation. If the rotatable eye selector knob 100 is actuated, the mirror 210 can then be rotated through ninety degrees so that the right eye and pupil can then be imaged for comparison purposes or for further characterization and sizing. Normally, stimulus diodes 140 are energized on the eyepiece of the eye to be measured. The controlling software, however, allows selection of the stimulus diodes facing the non-measured or contralateral eye. This permits measurement of so-called consensual stimulus which is of value in neuro-ophthalmological examinations.

The OpticRAMs have 256 pixels vertically and horizontally, and are rectangular rather than square since the pixels are larger in one direction. The good data diodes 80 operate primarily as an aid to alignment along the shorter axis of the rectangular image area. In a preferred embodiment, the IS32A OpticRAMs are an array of pixels 256 rows high by 256 columns wide. To determine the diameter of the image, the pixels are read for each row from rows 1 through row 256, to determine the number of dark pixels. This is considered to be the length of the chord bisecting the pupil image at that point. The longest chord is then considered to be the diameter. If the longest chord is found in the first 64 rows (row 1 through 64) or the last 64 rows (row 192 through 256) of the pupil image then the corresponding good diode 80 is turned off to indicate to the user that the user's pupil should move in the direction of the lighted one in order to better center the image on the OpticRAM 220. If the pupil image is displaced enough so that its diameter is not on the OpticRAM 220, both light-emitting diodes 80 are lit. Under those circumstances, the subject will see that the target 100 is off center by an appreciable amount and will move to correct that error.

A distinct advantage of the present invention utilizing the semi-passive target 60 is that this simple target eliminates the need for liquid crystal display panels and drive systems which are found in the Carter '506 patent, for example. This allows the electronics which drive the system to be placed on a small PC board mounted directly on optical block 40 which carries the scanner electronics, the light-emitting diode selection and drive elements, and jacks into which the IS32A OpticRAM and light-emitting diode cables must be interfaced. That circuitry is designed to operate on the 5 volt power available from so-called notebook or lap-top computers through an interface packaged as a PCMCIA driver card.

Figure 5B:
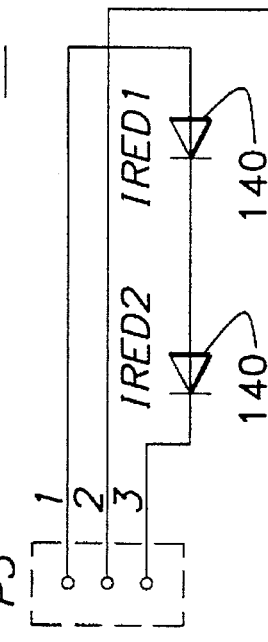
FIGS. 5A and 5B are circuit schematics for the diode rings containing infrared emitting diodes (IREDs) and high intensity green stimulus diodes in the binocular eye pieces of pupillometers provided in accordance with the present invention.
Figure 5B:
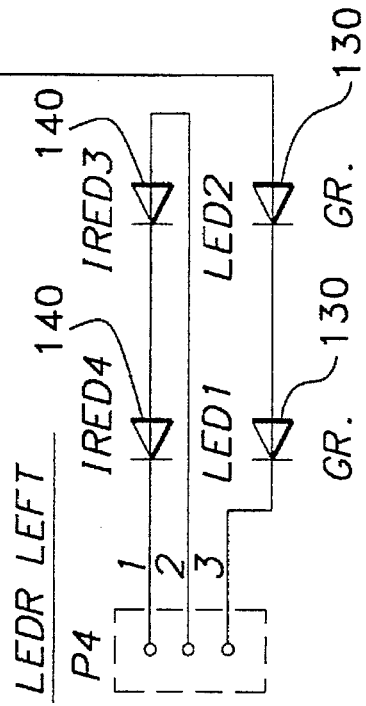
Figure 5A:
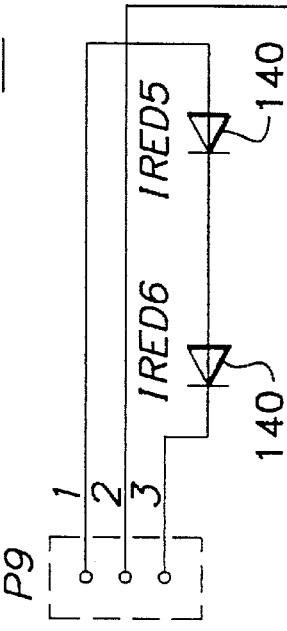
Figure 5A:
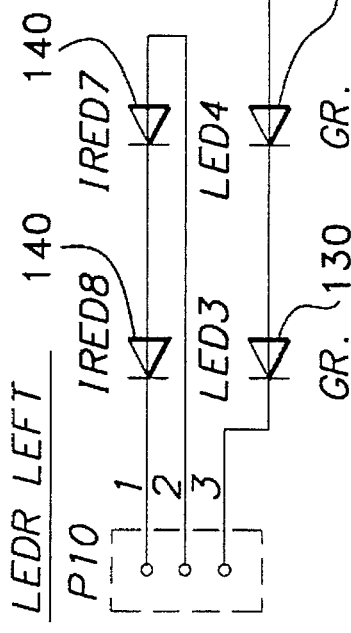
Figure 6B:
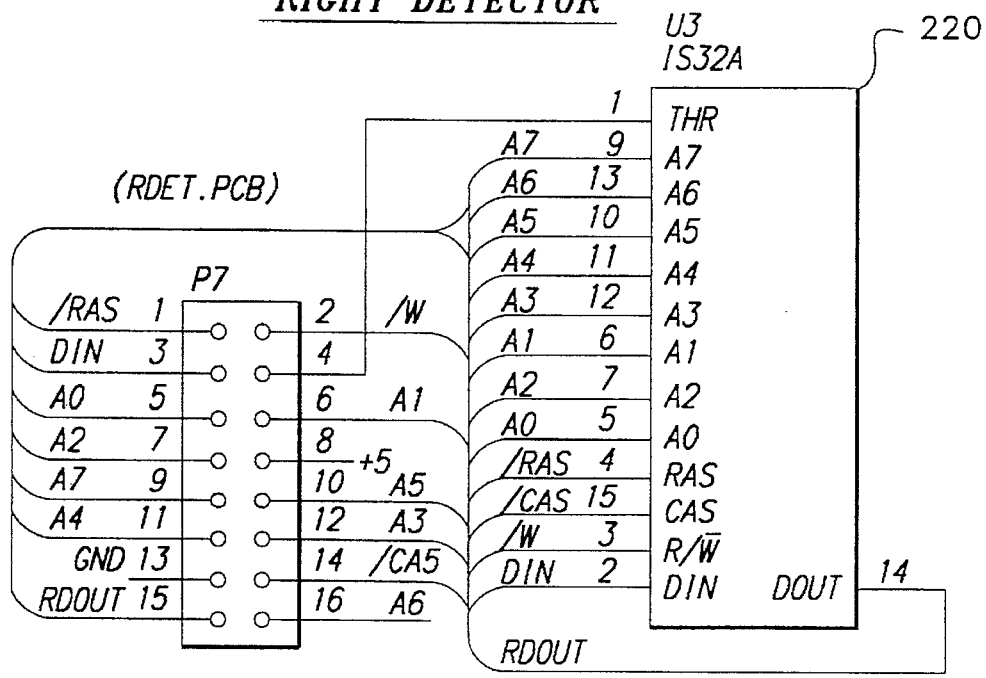
FIGS. 6A and 6B are schematics of the left and right detection circuits of pupillometers provided in accordance with the present invention.
Figure 6A:
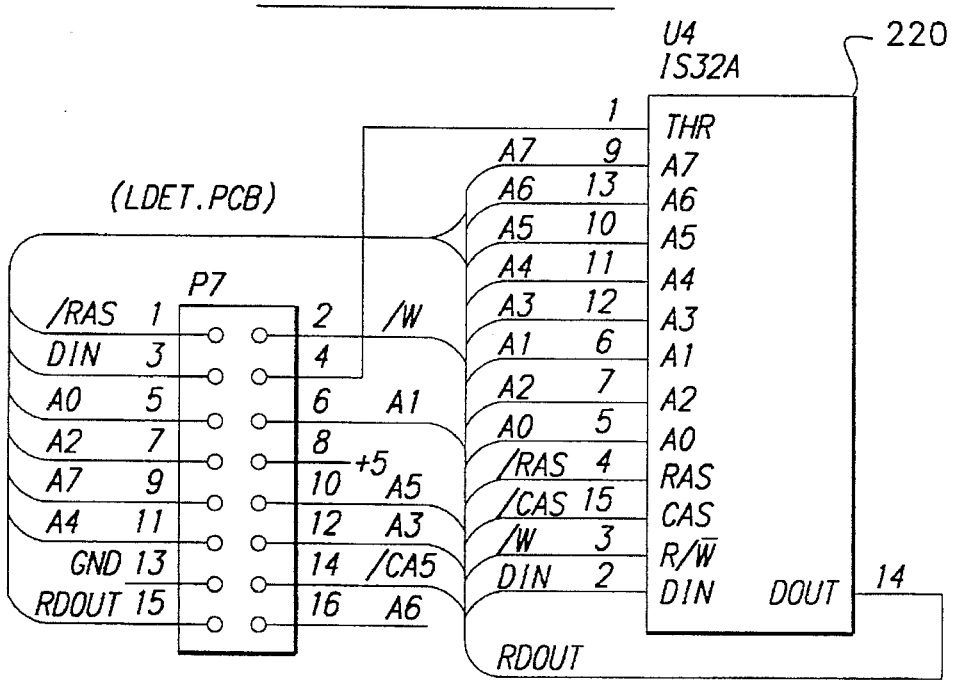

Referring to FIGS. 4A–4D, FIGS. 5A–5B and 6A–6B, the electronics for driving the pupillometer provided in accordance with the present invention and for imaging are illustrated. FIGS. 4A–4D are the scanning circuit on the optical block 40 circuit board described above. FIGS. 5A–5B are the left and right eye position circuits containing the various diodes which scan and stimulate the pupils. FIGS. 6A and 6B are the left and right detectors interfaced to the IS32A OpticRAMs (U4 and U3) that image the pupils.

On the scanning circuit board, integrated circuit U1 is an electronic programmable gate array which is preferably an EPM 7064 chip shown generally at 230 that controls operation of the pupillometer. EPM 230 is interfaced to the computer 50 through the plug P1 at 250, FIG. 4B at 240 which provides a 14.318 megahertz clock signal to drive the scanning circuits. The output of EPM 230 is bussed to the rest of the circuits, particularly the eye positioning circuits and eye detecting circuits, as well as the red diodes 80 on the semi-passive target 60.

The user tells the computer which eye is to be tested and rotates the mirror 210 for that eye. The user then positions that eye to view the target 60 through the optical block 40 and depresses the switch 70. That tells the computer to start the scanning, turning on the selected (left or right) IREDs 130 and the IS32A detector 220 through the EPM 230. The detectors 220 are connected to the EPM 230 scanning controller through the jumper blocks J8/P8 and J7/P7 respectively so that the pixel data from the selected IS32A OpticRAM 220 can be fed back to the computer though the interface card 55 for analysis. Note that all the signals to and from the computer pass through the P1 plug at 250.

The good data LEDs 80 in the target 60 are connected to the controller EPM 230 through the jumper block J5/P5. The computer drives them through the controller as described earlier depending on the user's eye position. The user keeps the switch 70 depressed until the eye is positioned to cause the good data LEDs to stay lit. At that point the user releases the switch 70, and the computer flashes the green stimulus LEDs 140 through the controller EPM 230 and captures the subsequent pixel/pupil images (at 10 or 20 per second) as the pupil constricts and re-dilates, extracting and recording each pupil diameter. During that period the user maintains his or her head and eye position to keep the good data LEDs 80 lit.

Laptop or notebook computers normally can supply power only at 5 volts through the PCMCIA interface card 55. That requires the four infrared-emitting diodes 130 in each ring 90 to be driven as two pairs. FIGS. 5A and 5B. The controller 230 turns on the hexfets Q5, Q6 if the right eye is selected, or the Q7, Q8 units for the left eye, switching the 5 volt power to the selected ring 90 in FIG. 4B. The infrared diodes 130 in the right eye ring 90 are connected through the jumper blocks J3/P3 and J4/P4 (FIGS. 4D and 5B) to the drive transistors Q1, Q2. If the right eye is selected Q5, FIG. 4B, supplies power to drive transistors Q1, Q2, in FIG. 4D. The infrared diode current demanded by the computer is supplied through pin 6 of the connector P1 at 250. That current is pulled through IREDs 1, 2 and the transistor Q2 (through pin 3 of J3/P3). Transistors Q1 and Q2 are connected in a "current mirror" configuration so that an equal current is driven through the IREDs 3 and 4 (and R5 and D1 to ground). Q3 and Q4 form a current mirror for the left ring 90 infrared diodes if the left eye is selected, the 5 volt power being supplied by Q7.

The green stimulus diode current demanded by the computer is supplied through pin 8 of the connector P1 at 250. That current is pulled through pin 3 of J4/P4 or J10/P10 and the connected diode pair. Power is supplied to the selected ring 90 by Q6 or Q8 through pin 2 of J3/P3 or J9/P9.

The pupillometers provided in accordance with the present invention thus provide reduced electronic circuitry for pupil characterization, imaging and sizing, as well as an efficient semi-passive targeting mechanism for simple pupil centering on the optical elements which perform imaging. The pupillometer circuits and centering devices described and claimed herein greatly reduce the cost of scanning pupillometers over that which have heretofore existed, and reduce assembly and manufacturing costs for these devices. Such results have not heretofore been achieved in the art.

There have thus been described certain preferred embodiments of pupillometers with semi-passive targets, and methods of imaging pupils provided in accordance with the present invention. While preferred embodiments have been described and disclosed, it will be recognized by those with skill in the art that modifications are within the true spirit and scope of the invention. The appended claims are intended to cover all such modifications.

What is claimed is:

1. A portable pupillometer comprising:

a passive target which allows a user of the portable pupillometer to center the user's pupil on an optically sensitive element in the pupillometer so that the pupillometer can characterize the pupil; and a set of centering diodes disposed on the passive target which are activated by on optico-electronic means to give the user an indication that the pupil has been centered on the optically sensitive element when the user has centered the pupil on a defined portion of the passive target.

2. The portable pupillometer recited in claim 1 wherein the passive target further comprises a thin sheet having a target image printed thereon.

3. The pupillometer recited in claim 1 further comprising an optic block and integral electronic circuit board for processing data signals from the user's pupil for characterizing or imaging the pupil.

4. The pupillometer recited in claim 3 wherein the optical block further comprises binocular eyepieces having interfaced thereon stimulus diodes for stimulating the user's pupil to constrict.

5. The pupillometers recited in claim 4 further comprising a front surface rotatable mirror mounted in an optical path between the target and the binocular eyepieces which is rotatable so that the user can choose whether the right or left pupil will be imaged or characterized by the pupillometer.

6. A method of characterizing a pupil comprising the steps of:

focussing the eye containing the pupil on a passive target;

activating an indicator mechanism which will indicate that the pupil is adequately centered on the passive target; and irradiating the pupil with characterizing radiation when the indicator mechanism indicates that the pupil is centered.

7. The method recited in claim 6 wherein the passive target comprises a thin sheet with a printed target image thereon.

8. The method recited in claim 6 wherein the irradiating step comprises the step of irradiating the pupil with infrared radiation.

9. The method recited in claim 8 wherein the activating step comprises the step of turning on a set of red diodes to provide a reference for the user to center the eye on the passive target.

10. A pupillometer comprising:

optical means for busing light to a user's pupil; and opto-electronic centering means for enabling the user to center an image of the pupil on an element in the optical means.

11. The pupillometer of claim 10, further comprising target means in optical contact with the optical means and further interfaced with the centering means for providing an orientation for the user when the user observes the centering means, thereby allowing the user to center the image of the pupil on the element in the optical means.

12. The pupillometer recited in claim 11 wherein the target means is a passive target.

13. The pupillometer recited in claim 12 wherein the passive target comprises a thin sheet which has a target image printed thereon.

14. The pupillometer recited in claim 11 wherein the centering means further comprises a set of light-emitting diodes.

15. The pupillometer recited in claim 14 wherein the optical means comprises binocular eyepieces interfaced to each of the user's eyes and a set of barrels interfaced to each of the binocular eyepieces to focus the user's eyes on the target.

16. The pupillometer recited in claim 10 further comprising a rotatable mirror interfaced to the optical means which is rotatable by the user so that the user can choose an eye for imaging or characterization.

17. The pupillometer recited in claim 10 further comprising a personal computer interfaced to the optical means for controlling operation of the pupillometer.

18. The pupillometer recited in claim 17 wherein the computer interfaces with a Personal Computer Memory Card International Association circuit board containing timing and control electronics to operate the pupillometer.

* * * * *